(12) United States Patent
Ono et al.

(10) Patent No.: US 10,689,682 B2
(45) Date of Patent: *Jun. 23, 2020

(54) MOGROL GLYCOSYLTRANSFERASE AND GENE ENCODING SAME

(71) Applicant: SUNTORY HOLDINGS LIMITED, Osaka (JP)

(72) Inventors: Eiichiro Ono, Kyoto (JP); Misa Ochiai, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/538,046

(22) Filed: Aug. 12, 2019

(65) Prior Publication Data

US 2019/0367961 A1 Dec. 5, 2019

Related U.S. Application Data

(63) Continuation of application No. 15/519,326, filed as application No. PCT/JP2015/079907 on Oct. 16, 2015, now Pat. No. 10,407,706.

(30) Foreign Application Priority Data

Oct. 17, 2014 (JP) ................. 2014-213063

(51) Int. Cl.
*C12P 19/56* (2006.01)
*C12P 19/18* (2006.01)
(Continued)

(52) U.S. Cl.
CPC ............. *C12P 33/20* (2013.01); *C07J 9/00* (2013.01); *C07J 17/005* (2013.01); *C12N 1/16* (2013.01);
(Continued)

(58) Field of Classification Search
None
See application file for complete search history.

(56) References Cited

U.S. PATENT DOCUMENTS 10,407,706 B2 * 9/2019 Ono .................. C12P 33/20
2014/0308698 A1 10/2014 Liu et al.
(Continued)

FOREIGN PATENT DOCUMENTS

| CN | 104404065 A | 3/2015 |
|----|-------------|--------|
| EP | 3 191 584 | 7/2017 |
| WO | 2013/076577 A1 | 5/2013 |

OTHER PUBLICATIONS

UniProt Accession No. F6HAY4_VITVI, published Jul. 27, 2011 (Year: 2011).*

(Continued)

*Primary Examiner* — Richard C Ekstrom
(74) *Attorney, Agent, or Firm* — Greenblum & Bernstein, P.L.C.

(57) ABSTRACT

To provide a mogrol glycosyltransferase and a method for producing a mogrol glycoside using the enzyme. The present invention provides a mogrol glycosyltransferase and a method for producing a mogrol glycoside using the enzyme, and a transformant into which a mogrol glycosyltransferase gene is introduced and a method for preparing the transformant.

19 Claims, 4 Drawing Sheets

Specification includes a Sequence Listing.

(51) Int. Cl.
| | |
|---|---|
| C12P 33/00 | (2006.01) |
| C12P 33/20 | (2006.01) |
| C12N 15/52 | (2006.01) |
| C12N 15/63 | (2006.01) |
| C12N 1/16 | (2006.01) |
| C12N 1/20 | (2006.01) |
| C07J 9/00 | (2006.01) |
| C07J 17/00 | (2006.01) |

(52) U.S. Cl.
CPC .............. *C12N 1/20* (2013.01); *C12N 15/52* (2013.01); *C12N 15/63* (2013.01); *C12P 19/18* (2013.01); *C12P 19/56* (2013.01); *C12P 33/00* (2013.01); *C12Y 204/01* (2013.01)

(56) References Cited

U.S. PATENT DOCUMENTS

| | | | |
|---|---|---|---|
| 2015/0064743 A1 | 3/2015 | Liu et al. | |
| 2017/0275666 A1* | 9/2017 | Prakash | ................. C12P 19/56 |
| 2017/0283844 A1 | 10/2017 | Itkin et al. | |
| 2017/0335362 A1* | 11/2017 | Ono | ....................... C07J 17/005 |

OTHER PUBLICATIONS

Extended European Search Report issued in EP Patent Application No. 15850103.1, dated Jun. 4, 2018.

Tang et al., "An efficient approach to finding *Siraitia grosvenorii*triterpene biosynthetic genes by RNA-seq and digital gene expression analysis", *BMC Genomics*, vol. 12, No. 343, pp. 1-13 (2011).

Bowles et al., "Glycosyltransferases: managers of small molecules", *Curr. Opin. Plant Biol.*, vol. 8, No. 3, pp. 254-263 (2005).

Database DDBJ/EMBL/GenBank [online] Accession No. JL532008, May 31, 2012 uploaded, [retrieval date Dec. 12, 2015] Internet: <http://www.ncbi.nlm.nih.gov/nuccore/j1532008>, Definition: TSA: Siraitia grosvenorii SIG_007830 mRNA sequence.

Kasai, R. "Studies on the Constituents of Cucurbitaceous Plants." Yakugaku Zasshi 128(10), pp. 1369-1382 (2008), including English language Abstract.

Ukiya et al., "Inhibitory Effects of Cucurbitane Glycosides and Other Triterpenoids from the Fruit of *Momordica grosvenori* on Epstein-Barr Virus Early Antigen Induced by Tumor Promoter 12-O-Tetradecanoylphorbol-13-acetate", *J. Agric. Food. Chem.*, vol. 50, pp. 6710-6715 (2002).

International Search Report issued in PCT/JP2015/079907, dated Dec. 22, 2015, along with an English language translation.

* cited by examiner

SEQUENCE LISTING

```
<160> NUMBER OF SEQ ID NOS: 2

<210> SEQ ID NO 1
<211> LENGTH: 1374
<212> TYPE: DNA
<213> ORGANISM: Siraitia grosvenorii
<220> FEATURE:
<221> NAME/KEY: CDS
<222> LOCATION: (1)..(1371)

<400> SEQUENCE: 1 atg ggt ggt cgt gaa ggt aaa gtt cat gtt ctg gtt gtt ctg ttt ccg      48
Met Gly Gly Arg Glu Gly Lys Val His Val Leu Val Val Leu Phe Pro
1               5                   10                  15 gat ggt cag ggt cat att aat ccg att ctg cag ttt agc aaa cgc ctg      96
Asp Gly Gln Gly His Ile Asn Pro Ile Leu Gln Phe Ser Lys Arg Leu
            20                  25                  30 gca ttt aaa ggt ctg gca gtt acc ctg ctg aat gtt ttt cgt agc caa     144
Ala Phe Lys Gly Leu Ala Val Thr Leu Leu Asn Val Phe Arg Ser Gln
        35                  40                  45 gaa agc cat acc ctg aat ctg cat ccg agc att aat gtt gaa cat cgt     192
Glu Ser His Thr Leu Asn Leu His Pro Ser Ile Asn Val Glu His Arg
    50                  55                  60 ccg cgt ctg ccg tat cag ggc acc gaa ccg gaa agc ctg gaa agc cac     240
Pro Arg Leu Pro Tyr Gln Gly Thr Glu Pro Glu Ser Leu Glu Ser His
65                  70                  75                  80
```

```
atg cat cgt ctg caa acc agc att tgt ttt cac atg acc aaa ctg att      288
Met His Arg Leu Gln Thr Ser Ile Cys Phe His Met Thr Lys Leu Ile
                85                  90                  95 agc cat cat cag agc agc ggt agc ccg att gca tgt gtt gtt tat gat      336
Ser His His Gln Ser Ser Gly Ser Pro Ile Ala Cys Val Val Tyr Asp
                100                 105                 110 agc gtt acc ccg tgg gtt ctg gat gtt gca aaa ggt ttt ggt gtt ccg      384
Ser Val Thr Pro Trp Val Leu Asp Val Ala Lys Gly Phe Gly Val Pro
            115                 120                 125 ggt gca ccg ttt ttt acc gaa agc agc gca gtt aat gcc atc ttt tat      432
Gly Ala Pro Phe Phe Thr Glu Ser Ser Ala Val Asn Ala Ile Phe Tyr
        130                 135                 140 cat gtt cat cgt ggc tgg ctg aaa att ccg att gat gat agc agc gtt      480
His Val His Arg Gly Trp Leu Lys Ile Pro Ile Asp Asp Ser Ser Val
145                 150                 155                 160 agc ctg cct ggt ctg ccg ctg ctg cag att agc gat ctg ccg agc atg      528
Ser Leu Pro Gly Leu Pro Leu Leu Gln Ile Ser Asp Leu Pro Ser Met
                165                 170                 175 att ccg aat ccg cag cag tat ccg att ttt ctg cgc ctg atg att gat      576
Ile Pro Asn Pro Gln Gln Tyr Pro Ile Phe Leu Arg Leu Met Ile Asp
                180                 185                 190 cag ttt tcc aat aaa ccg gac tgg atg ttt atc aac acc ttt aat agc      624
Gln Phe Ser Asn Lys Pro Asp Trp Met Phe Ile Asn Thr Phe Asn Ser
            195                 200                 205 ctg gaa ccg gaa gtt ctg cag tgg att cag acc cat aca ccg ctg aaa      672
Leu Glu Pro Glu Val Leu Gln Trp Ile Gln Thr His Thr Pro Leu Lys
        210                 215                 220 acc gtt ggt ccg acc gtt ccg agt att att acc gat aaa cgt ctg aaa      720
Thr Val Gly Pro Thr Val Pro Ser Ile Ile Thr Asp Lys Arg Leu Lys
225                 230                 235                 240 gat gat cag cat tat ggc atc gac ctg ttt aaa agc acc ggt gat gaa      768
Asp Asp Gln His Tyr Gly Ile Asp Leu Phe Lys Ser Thr Gly Asp Glu
                245                 250                 255 atc aaa acc atc gaa tgg ctg gat agc aaa gat agc ggt agc gtt att      816
Ile Lys Thr Ile Glu Trp Leu Asp Ser Lys Asp Ser Gly Ser Val Ile
                260                 265                 270 tat gtt agc ttt ggt agc gtg agc gat ctg ggc gaa gaa caa atg gaa      864
Tyr Val Ser Phe Gly Ser Val Ser Asp Leu Gly Glu Glu Gln Met Glu
            275                 280                 285 gaa ctg gca tgg ggt ctg aaa agc acc aat aaa agc ttt ctg tgg gtt      912
Glu Leu Ala Trp Gly Leu Lys Ser Thr Asn Lys Ser Phe Leu Trp Val
        290                 295                 300 gtt cgt gaa acc ggc acc agc aaa ctg ccg agt aat ctg ctg gaa gaa      960
Val Arg Glu Thr Gly Thr Ser Lys Leu Pro Ser Asn Leu Leu Glu Glu
305                 310                 315                 320 atg aaa gaa acc ggt atg gtt gtt aat tgg tgt agc cag ctg cag gtt     1008
Met Lys Glu Thr Gly Met Val Val Asn Trp Cys Ser Gln Leu Gln Val
                325                 330                 335 ctg gca cat aaa agc gtt ggt tgt ttt att acc cat tgc ggt tgg aat     1056
Leu Ala His Lys Ser Val Gly Cys Phe Ile Thr His Cys Gly Trp Asn
                340                 345                 350 agc gtt ctg gaa gca ctg agc ctg ggt att ccg atg gtt gca atg ccg     1104
Ser Val Leu Glu Ala Leu Ser Leu Gly Ile Pro Met Val Ala Met Pro
            355                 360                 365 cag tgg acc gat cag atg acc aat gca aaa ttt gtt gag gat gtt tgg     1152
Gln Trp Thr Asp Gln Met Thr Asn Ala Lys Phe Val Glu Asp Val Trp
        370                 375                 380 aaa gtt ggt gtt cgt gtt agc agc aaa gaa aat gca att gcc ggt cgc     1200
Lys Val Gly Val Arg Val Ser Ser Lys Glu Asn Ala Ile Ala Gly Arg
385                 390                 395                 400
```

```
gaa gaa att gaa ctg tgt att cgt cag gtt atg gaa ggt gaa cgt agc    1248
Glu Glu Ile Glu Leu Cys Ile Arg Gln Val Met Glu Gly Glu Arg Ser
            405                 410                 415 gca gaa atg cgt gaa aat gcg agc cgt tgg atg aaa ctg gca aaa gaa    1296
Ala Glu Met Arg Glu Asn Ala Ser Arg Trp Met Lys Leu Ala Lys Glu
        420                 425                 430 gca gtt gac gaa ggc ggt agc agc gat aaa aac att gat gaa ttt gtt    1344
Ala Val Asp Glu Gly Gly Ser Ser Asp Lys Asn Ile Asp Glu Phe Val
    435                 440                 445 gcc cag ctg acc aat cgc aat ccg aat taa                             1374
Ala Gln Leu Thr Asn Arg Asn Pro Asn
450                 455

<210> SEQ ID NO 2
<211> LENGTH: 457
<212> TYPE: PRT
<213> ORGANISM: Siraitia grosvenorii

<400> SEQUENCE: 2

Met Gly Gly Arg Glu Gly Lys Val His Val Leu Val Leu Phe Pro
1               5                   10                  15

Asp Gly Gln Gly His Ile Asn Pro Ile Leu Gln Phe Ser Lys Arg Leu
            20                  25                  30

Ala Phe Lys Gly Leu Ala Val Thr Leu Leu Asn Val Phe Arg Ser Gln
        35                  40                  45

Glu Ser His Thr Leu Asn Leu His Pro Ser Ile Asn Val Glu His Arg
    50                  55                  60

Pro Arg Leu Pro Tyr Gln Gly Thr Glu Pro Glu Ser Leu Glu Ser His
65                  70                  75                  80

Met His Arg Leu Gln Thr Ser Ile Cys Phe His Met Thr Lys Leu Ile
                85                  90                  95

Ser His His Gln Ser Ser Gly Ser Pro Ile Ala Cys Val Val Tyr Asp
            100                 105                 110

Ser Val Thr Pro Trp Val Leu Asp Val Ala Lys Gly Phe Gly Val Pro
        115                 120                 125

Gly Ala Pro Phe Phe Thr Glu Ser Ser Ala Val Asn Ala Ile Phe Tyr
    130                 135                 140

His Val His Arg Gly Trp Leu Lys Ile Pro Ile Asp Asp Ser Ser Val
145                 150                 155                 160

Ser Leu Pro Gly Leu Pro Leu Leu Gln Ile Ser Asp Leu Pro Ser Met
                165                 170                 175

Ile Pro Asn Pro Gln Gln Tyr Pro Ile Phe Leu Arg Leu Met Ile Asp
            180                 185                 190

Gln Phe Ser Asn Lys Pro Asp Trp Met Phe Ile Asn Thr Phe Asn Ser
        195                 200                 205

Leu Glu Pro Glu Val Leu Gln Trp Ile Gln Thr His Thr Pro Leu Lys
    210                 215                 220

Thr Val Gly Pro Thr Val Pro Ser Ile Ile Thr Asp Lys Arg Leu Lys
225                 230                 235                 240

Asp Asp Gln His Tyr Gly Ile Asp Leu Phe Lys Ser Thr Gly Asp Glu
                245                 250                 255

Ile Lys Thr Ile Glu Trp Leu Asp Ser Lys Asp Ser Gly Ser Val Ile
            260                 265                 270

Tyr Val Ser Phe Gly Ser Val Ser Asp Leu Gly Glu Glu Gln Met Glu
        275                 280                 285
```

```
Glu Leu Ala Trp Gly Leu Lys Ser Thr Asn Lys Ser Phe Leu Trp Val
    290             295             300
Val Arg Glu Thr Gly Thr Ser Lys Leu Pro Ser Asn Leu Leu Glu Glu
305             310             315                         320
Met Lys Glu Thr Gly Met Val Val Asn Trp Cys Ser Gln Leu Gln Val
                325             330                         335
Leu Ala His Lys Ser Val Gly Cys Phe Ile Thr His Cys Gly Trp Asn
            340             345             350
Ser Val Leu Glu Ala Leu Ser Leu Gly Ile Pro Met Val Ala Met Pro
        355             360             365
Gln Trp Thr Asp Gln Met Thr Asn Ala Lys Phe Val Glu Asp Val Trp
    370             375             380
Lys Val Gly Val Arg Val Ser Ser Lys Glu Asn Ala Ile Ala Gly Arg
385             390             395                         400
Glu Glu Ile Glu Leu Cys Ile Arg Gln Val Met Glu Gly Glu Arg Ser
                405             410             415
Ala Glu Met Arg Glu Asn Ala Ser Arg Trp Met Lys Leu Ala Lys Glu
            420             425             430
Ala Val Asp Glu Gly Gly Ser Ser Asp Lys Asn Ile Asp Glu Phe Val
        435             440             445
Ala Gln Leu Thr Asn Arg Asn Pro Asn
    450             455
```

MOGROL GLYCOSYLTRANSFERASE AND GENE ENCODING SAME

This application is a Continuation of U.S. patent application Ser. No. 15/519,326, filed Jul. 3, 2017, which is the National Stage of International Patent Application No. PCT/JP2015/079907, filed Oct. 16, 2015, which claims the benefit of priority of Japanese Application No. 2014-213063, filed Oct. 17, 2014. The disclosures of these documents, including the specifications, drawings and claims, are incorporated herein by reference in their entirety.

SEQUENCE LISTING

The instant application contains a Sequence Listing which has been submitted electronically in ASCII format and is hereby incorporated by reference in its entirety. Said ASCII copy, created on Jun. 30, 2017, is named P52104_SL.TXT and is 11,074 bytes in size.

TECHNICAL FIELD

The present invention relates to a protein having an activity of synthesizing a mogrol glycoside and a polynucleotide encoding the same; a method for producing a mogrol glycoside using the protein; a transformant highly expressing a mogrol glycosyltransferase; and a mogrol glycoside prepared by the method and the use thereof.

BACKGROUND ART

The fruit of Cucurbitaceae plants contains a series of compounds called mogrosides which are glycosides of mogrol as a triterpene phytosterol. These mogrosides have the degree of sweetness several hundred times that of sucrose and have good quality of taste; thus, they are expected as alternative sweeteners for reduced-calorie foods like rebaudioside as a glycoside of a diterpene steviol in Asteraceae *stevia*.

For rebaudioside in *stevia*, rebaudioside A (a glycoside with 4 glucose residues added) and rebaudioside D (a glycoside with 5 glucose residues added), which are highly glycosylated, are estimated to be good in taste and have a high degree of sweetness. Similarly, for mogrol, one with 5 glucose residues added called mogroside V is good in sweetness and quality of taste and commercially available (Non Patent Literature 1). In addition, it is reported to have useful functionality other than that as a sweetener and is a plant metabolite receiving attention (Non Patent Literature 2). Meanwhile, it is unclear how a mogrol glycoside is biosynthesized in a plant body such as *Siraitia grosvenorii*.

NON-PATENT LITERATURES

Non-Patent Literature 1: Kasai, R. (2008) Studies on the constituent of Cucurbitaceous plants. YAKUGAKU ZASSGU 128(10), 1369-1382.

Non-Patent Literature 2: Ukiya, M., et al. (2002) Inhibitory Effects of Cucurbitane Glycosides and Other Triterpenoids from the Fruit of *Momordica grosvenori* on Epstein-Barr Virus Early Antigen Induced by Tumor Promoter 12-O-Tetradecanoylphorbol-13-acetate. J. Agric. Food. Chem. 50, 6710-6715. (Nihon University)

DISCLOSURE OF INVENTION

As a result of conducting intensive studies, the present inventors have succeeded in identifying an enzyme catalyzing sugar addition reaction to glucose at position 24 of a mogrol glycoside and a gene sequence encoding the enzyme. The present invention is based on the above findings.

Specifically, the present invention provides the followings:

[1]

A protein selected from the group consisting of the following (a) to (c):

(a) a protein consisting of the amino acid sequence of SEQ ID NO: 2;

(b) a protein consisting of an amino acid sequence in which 1 to 45 amino acids are deleted, substituted, inserted, and/or added in the amino acid sequence of SEQ ID NO: 2 and having an activity of adding a sugar molecule to an $R^1$ group at position 24 of a compound represented by the following formula (I); and (c) a protein having an amino acid sequence having 90% or more sequence identity with the amino acid sequence of SEQ ID NO: 2 and having the activity of adding a sugar molecule to an $R^1$ group at position 24 of the compound represented by the formula (I),

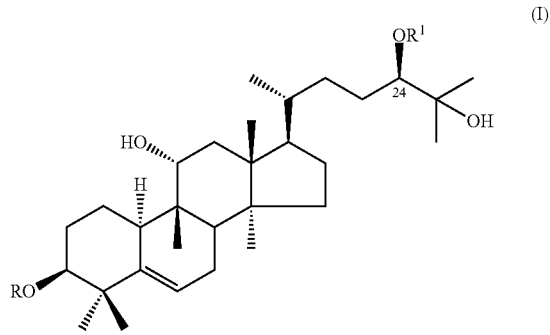

where R and $R^1$ are each independently represent H, a monosaccharide, or a disaccharide.

[2]

The protein according to [1] above, wherein the sugar molecule is a hexose.

[3]

The protein according to [1] above, wherein the sugar molecule is selected from the group consisting of glucose, mannose, and galactose.

[4]

The protein according to [1] above, wherein the R and $R_1$ are each independently H or a sugar residue of glucose monomer or glucose dimer.

[5]

The method according to [1] above, wherein the compound represented by the formula (I) is mogrol or a mogrol glycoside.

A polynucleotide selected from the group consisting of the following (a) to (e):

(a) a polynucleotide containing the nucleotide sequence of SEQ ID NO: 1;

(b) a polynucleotide encoding a protein consisting of the amino acid sequence of SEQ ID NO: 2;

(c) a protein consisting of an amino acid sequence in which 1 to 45 amino acids are deleted, substituted, inserted, and/or added in the amino acid sequence of SEQ ID NO: 2 and having an activity of adding a sugar molecule to an $R^1$ group at position 24 of a compound represented by the following formula (I); and (c) a protein having an amino acid sequence having 90% or more sequence identity with the amino acid sequence of SEQ ID NO: 2 and having the activity of adding a sugar molecule to an $R^1$ group at position 24 of the compound represented by the formula (I),

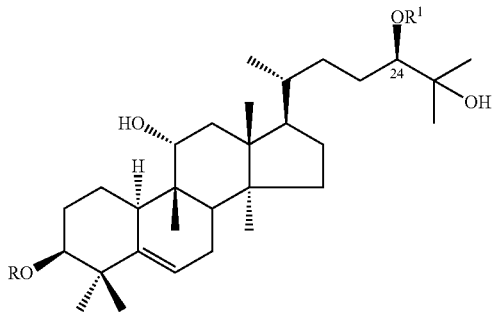

where R and $R^1$ each independently represent H, a monosaccharide, or a disaccharide.

[7]

The polynucleotide according to [6] above, wherein the sugar molecule is a hexose.

[8]

The polynucleotide according to [6] above, wherein the sugar molecule is selected from the group consisting of glucose, mannose, and galactose.

[9]

The polynucleotide according to [6] above, wherein the R and $R^1$ are each independently H or a sugar residue of glucose monomer or glucose dimer.

[10]

The polynucleotide according to [6] above, wherein the compound represented by the formula (I) is mogrol or a mogrol glycoside.

[11]

A non-human transformant into which the polynucleotide according to [6] above is introduced.

[12]

The transformant according to [11] above, wherein the polynucleotide is one inserted into an expression vector.

[13]

The transformant according to [11] above, wherein the transformant is a plant body.

An extract of the transformant according to [11] above.

[15]

A food, a pharmaceutical product, or an industrial raw material comprising the extract according to [14] above.

[16]

A method for producing a protein, comprising culturing the non-human transformant according to [11] above, wherein the protein has an activity of adding a sugar molecule to an $R^1$ group at position 24 of a compound represented by the following formula (I):

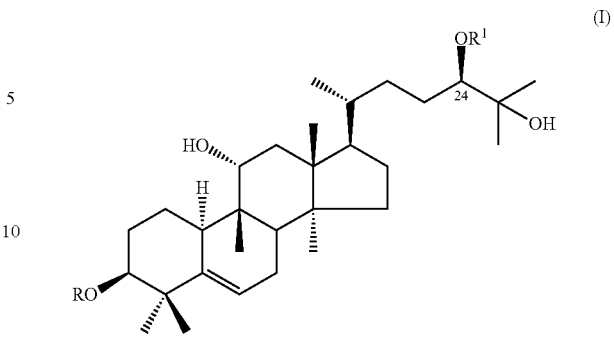

where R and $R_1$ each independently represent H, a monosaccharide, or a disaccharide.

[17]

A method for producing a mogrol glycoside, wherein the non-human transformant according to [11] above is used.

The method according to [17] above, wherein the mogrol glycoside is mogroside IA, mogroside Ib, mogroside IE, mogroside IIA, mogroside $IIA_1$, mogroside IIE, mogroside III, mogroside $IIIA_1$, mogroside $IIIA_2$, mogroside IIIE, mogroside IV, mogroside IVA, mogroside V, siamenoside I, 11-oxomogroside V, mogrol pentaglycoside, or a combination thereof.

[19]

A method for producing a mogrol glycoside, comprising a step of reacting the protein according to [1] above, a UDP-sugar, and a compound represented by the following formula (I):

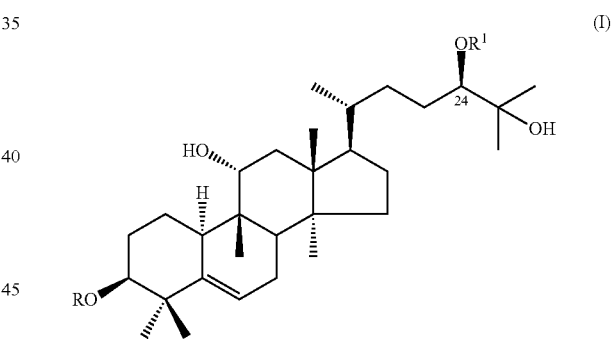

where R and $R^1$ each independently represent H, a monosaccharide, or a disaccharide.

[20]

The method according to [19] above, wherein the sugar in the UDP-sugar is glucose.

The method according to [19] above, wherein the mogrol glycoside is mogroside IA, mogroside Ib, mogroside IE, mogroside IIA, mogroside $IIA_1$, mogroside IIE, mogroside III, mogroside $IIIA_1$, mogroside $IIIA_2$, mogroside IIIE, mogroside IV, mogroside IVA, mogroside V, siamenoside I, 11-oxomogroside V, mogrol pentaglycoside, or a combination thereof.

By using the protein of the present invention and a polynucleotide encoding the protein, a mogrol glycoside (for example, mogroside V) is produced with a high efficiency. The transformant of the present invention has a high content of a mogrol glycoside (for example, mogroside V); thus, the mogrol glycoside (for example, mogroside V) can be efficiently extracted and purified from the transformant.

BEST MODE FOR CARRYING OUT THE INVENTION

The present invention will be described below in detail. The following embodiment is only illustrative for describing the present invention and is not intended to limit the invention only to the embodiment. The present invention may be embodied in various forms without departing from its subject matter.

All references and laid-open application publications, patent publications, and other patent literatures cited in the present specification are intended to be incorporated herein by reference. The present specification includes the contents described in the specification and drawings of Japanese Patent Application No. 2014-213063, filed Oct. 17, 2014, on which the priority of the present application is based.

Figure 1:
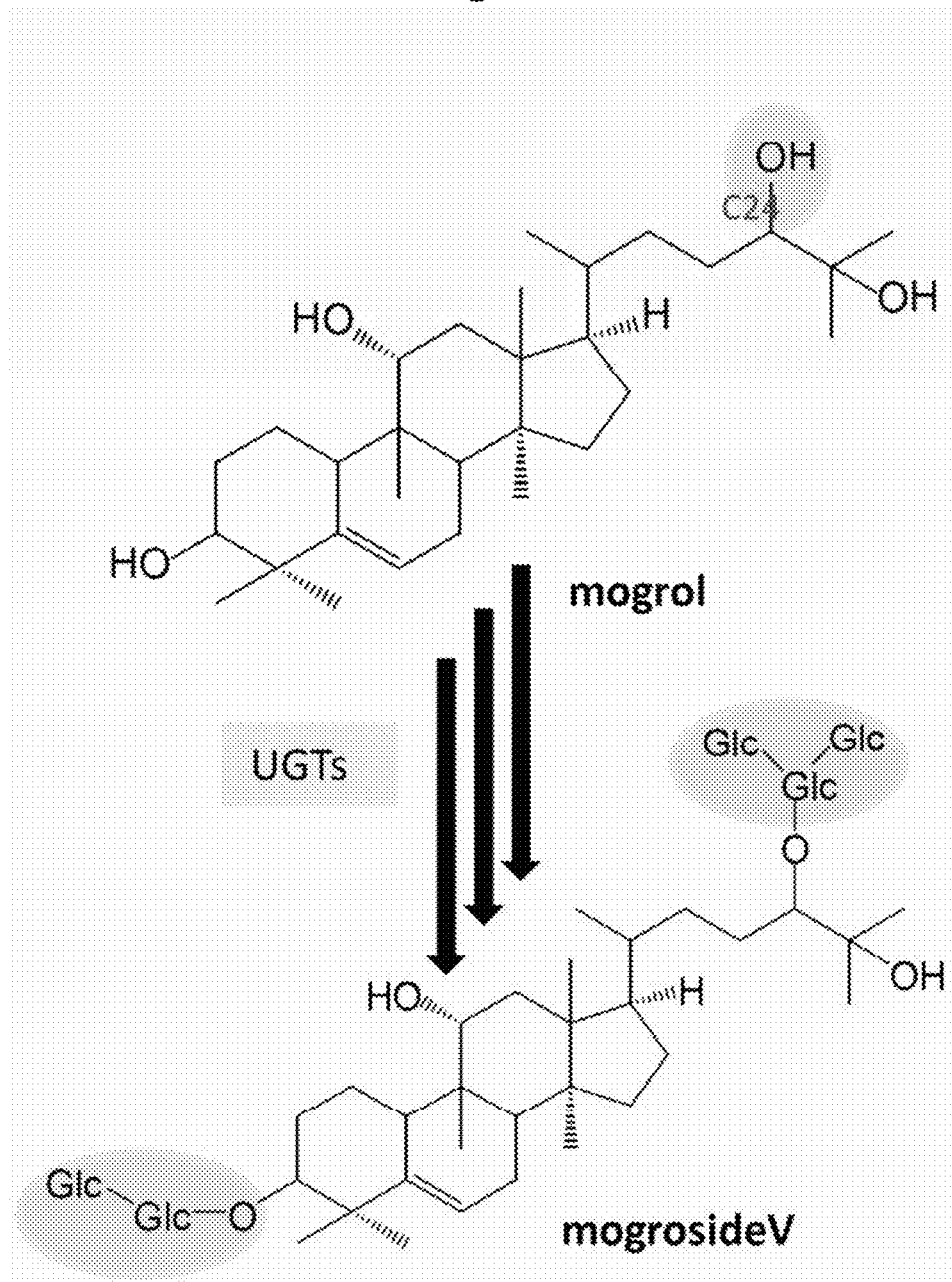
FIG. 1 is a diagram showing the formation of mogroside V as a glycoside where a glucose is added to mogrol by UGT enzyme.

The present inventors have first established that an enzyme of Cucurbitaceae *Siraitia grosvenorii*, SgUGT74G1_943, adds a glucose molecule to position 24 of mogrol or a mogrol glycoside (that is, has a glycosylation activity) (FIG. 1).

The CDS sequence and the deduced amino acid sequence of SgUGT74G1_943 are SEQ ID NOS: 1 and 2, respectively. The polynucleotide and the enzyme can be obtained, for example, by the technique described in Examples set forth hereinafter, a known genetic engineering technique, or a known synthesis technique.

1. Mogrol Glycosyltransferase

The present invention provides a protein selected from the group consisting of the following (a) to (c) (hereinafter referred to as "protein of the present invention"):

(a) a protein consisting of the amino acid sequence of SEQ ID NO: 2;

(b) a protein consisting of an amino acid sequence in which 1 to 45 amino acids are deleted, substituted, inserted, and/or added in the amino acid sequence of SEQ ID NO: 2 and having an activity of adding a sugar molecule to an $R^1$ group at position 24 of a compound represented by the following formula (I):

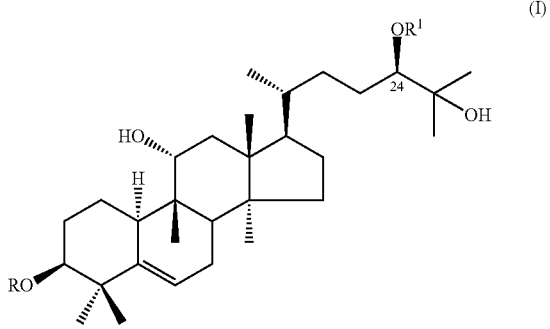

where R and $R^1$ each independently represent H, a monosaccharide, or a disaccharide; and (c) a protein having an amino acid sequence having 90% or more sequence identity with the amino acid sequence of SEQ ID NO: 2 and having the activity of adding a sugar molecule to an $R^1$ group at position 24 of the compound represented by the formula (I).

The protein described in (b) or (c) above is typically a variant of the naturally occurring polypeptide of SEQ ID NO: 2; however, the protein also includes those artificially obtainable by using a site-directed mutagenesis method as described, for example, in "Sambrook & Russell, Molecular Cloning: A Laboratory Manual Vol. 3, Cold Spring Harbor Laboratory Press 2001", "Ausubel, Current Protocols in Molecular Biology, John Wiley & Sons 1987-1997", "Nuc. Acids. Res., 10, 6487 (1982)", "Proc. Natl. Acad. Sci. USA, 79, 6409 (1982)", "Gene, 34, 315 (1985)", "Nuc. Acids. Res., 13, 4431 (1985)", or "Proc. Natl. Acad. Sci. USA, 82, 488 (1985)".

Examples of the "protein consisting of an amino acid sequence in which 1 to 45 amino acids are deleted, substituted, inserted, and/or added in the amino acid sequence of SEQ ID NO: 2 and having an activity of adding a sugar molecule to an $R^1$ group at position 24 of a compound represented by the formula (I)" herein include a protein consisting of an amino acid sequence in which, for example, 1 to 45, 1 to 44, 1 to 43, 1 to 42, 1 to 41, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, 1 to 2, or 1 amino acid residue is deleted, substituted, inserted, and/or added in the amino acid sequence of SEQ ID NO: 2 and having an activity of adding a sugar molecule to an $R^1$ group at position 24 of a compound represented by the formula (I). The smaller number of deletions, substitutions, insertions, and/or additions of the amino acid residues is typically more preferable.

Examples of such a protein include a protein having an amino acid sequence having a sequence identity of 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with the amino acid sequence of SEQ ID NO: 2 and having an activity of adding a sugar molecule to an $R^1$ group at position 24 of a compound represented by the formula (I). The larger numerical value of the sequence identity is typically more preferable.

Here, the "activity of adding a sugar molecule to an $R^1$ group at position 24 of a compound represented by the formula (I)" means an activity of adding a sugar to an $R^1$ group at position 24 of a compound represented by the following formula (I).

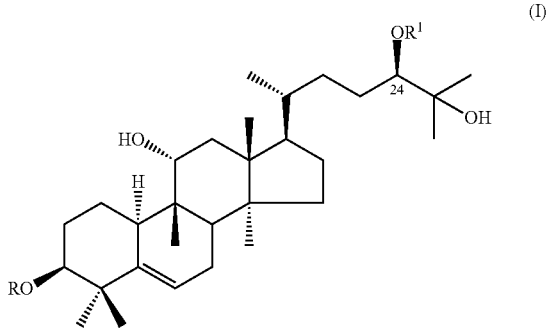

(I)

In the formula (I), R and $R^1$ each independently represent H, a monosaccharide, or a disaccharide. Here, the monosaccharide is not particularly limited.

"Monosaccharide" herein is not particularly limited; however, it may be a pentose or a hexose.

Examples of the pentose include ribose, arabinose, xylose, and lyxose, and examples of the hexose include allose, altrose, glucose, mannose, gulose, idose, galactose, and talose.

"Monosaccharide" may preferably be a hexose, more preferably a glucose monomer (-Glc).

"Disaccharide" herein is not limited provided that it is one formed by the binding of 2 monosaccharide molecules, and the combination of the 2 monosaccharide molecules may be any combination.

The monosaccharides constituting the disaccharide may preferably be both hexoses, and the disaccharide may more preferably be a glucose dimer (-Glc-Glc). In the disaccharide of a glucose dimer, the glucose molecules are preferably bound by a β2,1 glycosidic bond.

The compound of the formula (I) is preferably mogrol or a mogrol glycoside.

The sugar molecule added to an $R^1$ group at position 24 of a compound represented by the formula (I) by the protein of the present invention is not particularly limited; however, it may be a sugar molecule consisting of one or more pentoses or hexoses or a combination thereof. Examples of the pentose and the hexose are as described above. The sugar molecule is preferably a hexose, more preferably a hexose selected from the group consisting of glucose, mannose, and galactose. The sugar molecule is most preferably glucose.

The activity of adding a sugar molecule to an $R^1$ group at position 24 of a compound represented by the formula (I) can be verified by performing incubation in a buffer solution (for example, sodium phosphate buffer or potassium phosphate buffer), in the neutral pH range of 6.0 to 8.0, containing 1 to 500 ng (preferably 50 to 200 ng, most preferably 100 ng) of a test protein, 0.1 to 5 mM (preferably 1 to 3 mM, most preferably 2 mM) of a UDP-sugar (for example, UDP-glucose), and 0.1 to 3 mM (preferably 0.1 to 1 mM, most preferably 0.2 mM) of a substrate compound (a compound of the formula (I)) at a temperature of 20 to 40° C. for 10 minutes to 5 hours (preferably 1 to 3 hours, for example, 3 hours), followed by purifying the substrate compound and then analyzing the purified mogrol or mogrol glycosie using a known technique, such as LC-MS (Liquid Chromatography-Mass Spectrometry) analysis.

When a compound in which a sugar molecule is added to an $R^1$ group at position 24 of a compound represented by the formula (I) is detected as a result of the LC-MS analysis, the test protein can be said to have the activity of adding a sugar molecule to an $R^1$ group at position 24 of a compound represented by the formula (I).

The sugar addition reaction is typically completed in approximately 1 minute to 12 hours.

Deletion, substitution, insertion and/or addition of one or more amino acid residues in the amino acid sequence of the protein of the present invention is intended to mean that deletion, substitution, insertion and/or addition of one or more amino acid residues occurs at any one or more positions in the same sequence, and two or more of deletion, substitution, insertion and addition may occur at the same time.

Examples of interchangeable amino acid residues are shown below. Amino acid residues included in the same group are interchangeable with each other. Group A: leucine, isoleucine, norleucine, valine, norvaline, alanine, 2-aminobutanoic acid, methionine, o-methylserine, t-butylglycine, t-butylalanine, cyclohexylalanine; Group B: aspartic acid, glutamic acid, isoaspartic acid, isoglutamic acid, 2-aminoadipic acid, 2-aminosuberic acid; Group C: asparagine, glutamine; Group D: lysine, arginine, ornithine, 2,4-diaminobutanoic acid, 2,3-diaminopropionic acid; Group E: proline, 3-hydroxyproline, 4-hydroxyproline; Group F: serine, threonine, homoserine; Group G: phenylalanine, tyrosine.

Although the protein of the present invention may be obtained by being expressed from a polynucleotide encoding it (see "the polynucleotide of the present invention" described later) in appropriate host cells, it may also be prepared by chemical synthesis methods such as Fmoc method (fluorenylmethyloxycarbonyl method) and tBoc method (t-butyloxycarbonyl method). Alternatively, the protein of the present invention may also be chemically synthesized with peptide synthesizers commercially available from Advanced Automation Peptide Protein Technologies, Perkin Elmer, Protein Technologies, PerSeptive, Applied Biosystems, SHIMADZU, etc.

2. Method for Producing Mogrol Glycoside

The present invention can easily produce a large amount of a mogrol glycoside by use of the activity of adding a sugar molecule to an $R^1$ group at position 24 of a compound represented by the formula (I) which the protein has.

Accordingly, in another embodiment, the present invention provides a first method for producing a mogrol glycoside, including a step of adding a sugar molecule to an $R^1$ group at position 24 of a compound represented by the following formula (I) by reacting the protein of the present invention, a UDP-sugar, and a compound represented by the formula (I).

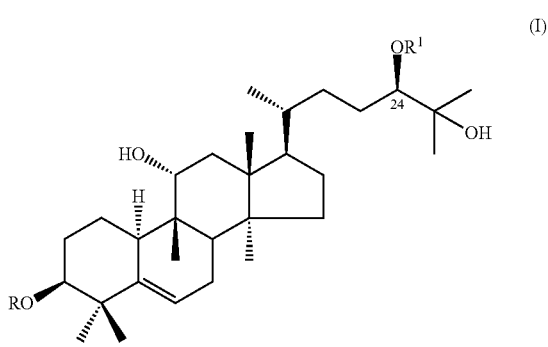

(I)

R and $R^1$ in the formula (I) are as defined above. The compound of the formula (I) is preferably mogrol or a mogrol glycoside.

"UDP-sugar" herein is a uridine diphosphate (UDP)-bound sugar. Preferred examples of the sugar part of the UDP-sugar include a sugar consisting of one or more pentoses or hexoses or a combination thereof. Examples of the pentose and the hexose are as described above. The UDP-sugar is preferably a UDP-hexose, and the sugar is more preferably a hexose selected from the group consisting of glucose, mannose, and galactose. The UDP-sugar is most preferably UDP-glucose.

The first method for producing a mogrol glycoside according to the present invention includes a step of reacting the protein of the present invention, a UDP-sugar, and a compound represented by the formula (I) to add the sugar molecule to an $R^1$ group at position 24 of the compound represented by the formula (I). The first production method of the present invention may further include a step of purifying the mogrol glycoside formed in the above step.

Examples of the mogrol glycoside formed by the first production method include, but not limited to, mogroside IA, mogroside Ib, mogroside IE, mogroside IIA, mogroside $IIA_1$, mogroside IIE, mogroside III, mogroside $IIIA_1$, mogroside $IIIA_2$, mogroside IIIE, mogroside IV, mogroside IVA, mogroside V, siamenoside I, 11-oxomogroside V, mogrol pentaglycoside, or a combination thereof.

The formed mogrol glycoside can be extracted using a suitable solvent (an aqueous solvent, such as water, or an organic solvent, such as alcohol, ether, or acetone) and purified by a known method, such as organic solvent (e.g. ethyl acetate): water gradient, high performance liquid chromatography (HPLC), gas chromatography, time-of-flight mass spectrometry (TOF-MS), or ultra (high) performance liquid chromatography (UPLC).

3. Non-Human Transformant Highly Containing Mogrol Glycoside

The mogrol glycoside may also be formed in cells of a microorganism (e.g. *E. coli* or yeast), a plant, an insect, or a mammal other than a human using the protein of the present invention. This is because the protein of the present invention is expected to have high activity even in the intracellular environment since it is a *Siraitia grosvenorii*-derived enzyme or its variant. In this case, the mogrol glycoside can be formed by expressing the protein of the present invention by introducing a polynucleotide encoding the protein of the present invention (see "Polynucleotide of the Invention" to be described later) into host cells derived, for example, from a microorganism, a plant, an insect, or a mammal other than a human, and reacting the protein of the present invention, a UDP-sugar present in the cells, and a compound represented by the formula (I).

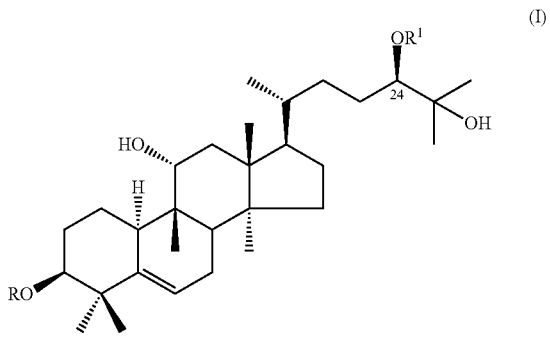

Accordingly, the present invention provides a non-human transformant into which a polynucleotide selected from the group consisting of the following (a) to (e) (hereinafter referred to as "polynucleotide of the present invention") is introduced (hereinafter referred to as "transformant of the present invention"):

(a) a polynucleotide containing the nucleotide sequence of SEQ ID NO: 1;

(b) a polynucleotide encoding a protein consisting of the amino acid sequence of SEQ ID NO: 2;

(c) a protein consisting of an amino acid sequence in which 1 to 45 amino acids are deleted, substituted, inserted, and/or added in the amino acid sequence of SEQ ID NO: 2 and having an activity of adding a sugar molecule to an $R^1$ group at position 24 of a compound represented by the formula (I);

(d) a polynucleotide encoding a protein having an amino acid sequence having 90% or more sequence identity with the amino acid sequence of SEQ ID NO: 2 and having the activity of adding a sugar molecule to an $R^1$ group at position 24 of the compound represented by the formula (I); and (e) a polynucleotide hybridizing to a polynucleotide consisting of a nucleotide sequence complementary to the nucleotide sequence of SEQ ID NO: 1 under highly stringent conditions, the polynucleotide encoding a protein having the activity of adding a sugar molecule to an $R^1$ group at position 24 of the compound represented by the formula (I).

The definition and specific examples of the formula (I) are as already described, and the definition and specific examples of the sugar molecule added to an $R^1$ group at position 24 of a compound represented by the formula (I) are also as described above.

"Polynucleotide" herein means DNA or RNA.

"Polynucleotide hybridizing under highly stringent conditions" herein refers to a polynucleotide obtained by use of, for example, a colony hybridization method, a plaque hybridization method, or a southern hybridization method using, for example, a polynucleotide consisting of a nucleotide sequence complementary to the nucleotide sequence of SEQ ID NO: 1 or all or part of a polynucleotide consisting of a nucleotide sequence encoding the amino acid sequence of SEQ ID NO: 2 as a probe. The hybridization method used may be a method as described, for example, in "Sambrook & Russell, Molecular Cloning: A Laboratory Manual Vol. 3, Cold Spring Harbor, Laboratory Press 2001" or "Ausubel, Current Protocols in Molecular Biology, John Wiley & Sons 1987-1997".

Examples of "highly stringent conditions" herein include, but not limited to, conditions of (1) 5×SSC, 5×Denhardt's solution, 0.5% SDS, 50% formamide, and 50° C., (2) 0.2×SSC, 0.1% SDS, and 60° C., (3) 0.2×SSC, 0.1% SDS, and 62° C., or (4) 0.2×SSC, 0.1% SDS, and 65° C. In these conditions, increasing the temperature can be expected to more efficiently provide DNA having high sequence identity. In this regard, possible factors affecting the stringency of hybridization are a plurality of factors, such as temperature, probe concentration, probe length, ionic strength, time, and salt concentration, and one skilled in the art can achieve similar stringency by properly selecting these factors.

When a commercially available kit is used for hybridization, Alkphos Direct Labelling and Detection System (GE Healthcare) can be used, for example. In this case, according to the protocol included in the kit, incubation with a labeled probe can be carried out overnight, followed by washing the membrane with a primary washing buffer containing 0.1% (w/v) SDS under conditions of 55 to 60° C. and then detecting the hybridized DNA. Alternatively, when a probe is prepared based on a nucleotide sequence complementary to the nucleotide sequence of SEQ ID NO: 1 or a sequence complementary to all or part of a nucleotide sequence encoding the amino acid sequence of SEQ ID NO: 2, the labeling of the probe with digoxigenin (DIG) using a commercially available reagent (for example, a PCR labeling mix (Roche Diagnostics K.K.)) enables the detection of hybridization using DIG Nucleic Acid Detection Kit (Roche Diagnostics K.K.).

Examples of hybridizable polynucleotides other than those described above can include DNA having a sequence identity of 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with DNA of SEQ ID NO: 1 or DNA encoding the amino acid sequence of SEQ ID NO: 2 when calculated with a homology search software, such as FASTA or BLAST, using default parameters.

The sequence identity of an amino acid sequence or a nucleotide sequence can be determined using FASTA (Science 227 (4693): 1435-1441 (1985)) or algorithm BLAST (Basic Local Alignment Search Tool) by Karlin and Altschul (Proc. Natl. Acad. Sci. USA 872264-2268, 1990; Proc. Natl. Acad. Sci. USA 90: 5873, 1993). Programs called balstn, blastx, blastp, tblastn, and tblastx based on the algorithm of BLAST have been developed (Altschul S F, et al.: J. Mol. Biol. 215: 403, 1990). In analyzing a nucleotide sequence using blastn, the parameters are set, for example, to score=100 and wordlength=12. In analyzing an amino acid sequence using blastp, the parameters are set, for example, to score=50 and wordlength=3. In using BLAST and Gapped BLAST programs, the default parameters of the respective programs are used.

The polynucleotide of the present invention described above can be obtained by a known genetic engineering technique or a known synthesis technique.

The polynucleotide of the present invention is preferably introduced into a host in a state inserted into a suitable expression vector.

The suitable expression vector is typically configured to include:

(i) a promoter capable of transcription in host cells;

(ii) the polynucleotide of the present invention, bound to the promoter; and (iii) an expression cassette containing signals functioning in the host cells for the transcription termination and polyadenylation of an RNA molecule, as constituents.

Examples of a method for preparing the expression vector include, but not particularly limited to, a method using a plasmid, a phage, or a cosmid.

The specific type of the vector is not particularly limited, and a vector capable of being expressed in host cells is properly selected. Specifically, a promoter sequence is properly selected to reliably express the polynucleotide of the present invention, depending on the type of host cells, and a vector in which the promoter sequence and the polynucleotide of the present invention are incorporated into any of various plasmids or the like may be used as the expression vector.

The expression vector of the present invention contains an expression control region (for example, a promoter, a terminator, and/or a replication origin), depending on the type of a host into which the vector is to be introduced. A conventional promoter (for example, trc promoter, tac promoter, or lac promoter) is used as an expression vector for bacteria; examples of a promoter for yeast include glyceraldehyde 3-phosphate dehydrogenase promoter and PH05 promoter; and examples of a promoter for filamentous bacteria include amylase and trpC. Examples of a promoter for expressing a target gene in plant cells include 35S RNA promoter of cauliflower mosaic virus, rd29A gene promoter, rbcS promoter, and mac-1 promoter in which an enhancer sequence in the 35S RNA promoter of cauliflower mosaic virus is added 5' to a mannopine synthase promoter sequence derived from Agrobacterium. Examples of a promoter for an animal cell host include viral promoters (for example, SV40 initial promoter and SV40 late promoter).

The expression vector preferably contains at least one selection marker. As such a marker, an auxotrophic marker (ura5, niaD), a drug-resistance marker (hygromycin, Zeosin), a geneticin resistance gene (G418r), a copper resistance gene (CUP1) (Marin et al., Proc. Natl. Acad. Sci. USA, vol. 81, p. 337, 1984), a cerulenin resistance gene (fas2m, PDR4) (in Junji Inokoshi et al., Seikagaku (Biochemistry), vol. 64, p. 660, 1992 and Hussain et al., Gene, vol. 101, p. 149, 1991, respectively), or the like can be used.

The method for preparing (method for producing) the transformant of the present invention is not particularly limited; however, examples thereof include a method involving introducing an expression vector containing the polynucleotide of the present invention into a host for transformation.

The transformant of the present invention is expected to contain a mogrol glycoside at a high content. The host cell used for transformation is not particularly limited and various known cells can preferably be used. Examples of the host cell include bacteria, such as *Escherichia coli*, yeast (*Saccharomyces cerevisiae* as budding yeast or *Schizosaccharomyces pombe* as fission yeast), plant cells, and cells of animals other than humans.

The host cell is not limited to one capable of forming a compound represented by the formula (I); however, the host cell is preferably a host cell capable of forming a compound represented by the formula (I). Here, the host cell may be one subjected to recombination with a known gene to be in a natural state, for example, to be capable of forming a compound represented by the formula (I).

Examples of a known gene encoding an enzyme contributing to the synthesis of a compound represented by the formula (I) include, but not limited to, a mogrol or mogroside synthesis-associated gene as described in cucurbitadienol synthase (M. Shibuya et al./Tetrahedron 60 (2004) 6995-7003).

When the host cell is one incapable of forming a compound represented by the formula (I), a compound represented by the formula (I) or a plant extract containing the compound can be added as a substrate to a culture system of the transformant obtained by introducing the gene of the present invention into the host cell to produce a mogrol glycoside without introducing a gene encoding an enzyme contributing to the synthesis of a compound represented by the formula (I).

Suitable culture media and conditions for the above host cells are well known in the art. The living organism to be transformed is not particularly limited; examples thereof include various microorganisms, plants, or animals other than humans exemplified in the above host cells.

As a method for transforming host cells, commonly used known methods can be used. The transformation can be carried out by, for example, but not limited to, an electroporation method (Mackenxie, D. A. et al., Appl. Environ.

Microbiol., vol. 66, p. 4655-4661, 2000), a particle delivery method (Japanese Patent Application Laid-Open No. 2005-287403), a spheroplast method (Proc. Natl. Acad. Sci. USA, vol. 75, p. 1929, 1978), a lithium acetate method (J. Bacteriology, vol. 153, p. 163, 1983), or a method as described in Methods in yeast genetics, 2000 Edition: A Cold Spring Harbor Laboratory Course Manual).

For other common molecular biological techniques, one may refer to, for example, "Sambrook & Russell, Molecular Cloning: A Laboratory Manual Vol. 3, Cold Spring Harbor Laboratory Press 2001", "Methods in Yeast Genetics, A laboratory manual (Cold Spring Harbor Laboratory Press, Cold Spring Harbor, N.Y.").

The culture of the transformant thus obtained enables the accumulation of a mogrol glycoside in the transformant. As described above, a compound of the formula (I) or a plant extract containing the compound can also be added as a substrate to a culture system of the transformant to promote the production of the mogrol glycoside. The accumulated mogrol glycoside can be extracted and purified to provide an intended mogrol glycoside.

Thus, the present invention provides a second method for producing a mogrol glycoside, comprising using the transformant of the present invention. Suitable culture media and conditions are well known in the art. The method for extracting and purifying the mogrol glycoside is as already described.

The mogrol glycoside is not particularly limited; however, the glycoside may preferably be one selected from the group consisting of mogroside IA, mogroside Ib, mogroside IE, mogroside IIA, mogroside $IIA_1$, mogroside IIE, mogroside III, mogroside $IIIA_1$, mogroside $IIIA_2$, mogroside IIIE, mogroside IV, mogroside IVA, mogroside V, siamenoside I, 11-oxomogroside V, mogrol pentaglycoside, and a combination thereof.

In one aspect of the present invention, the transformant can be a plant transformant. The plant transformant according to the present embodiment is obtained by introducing a recombinant vector containing the polynucleotide according to the present invention into a plant in such a way that a polypeptide encoded by the polynucleotide can be expressed.

When using a recombinant expression vector, the recombinant expression vector used for the transformation of a plant body is not particularly limited provided that it is a vector capable of expressing the polynucleotide according to the present invention in the plant. Examples of such a vector include a vector having a promoter constitutively causing the expression of a polynucleotide in plant cells, and a vector having a promoter inducibly activated by an external stimulus.

Examples of the promoter constitutively causing the expression of a polynucleotide in plant cells include 35S RNA promoter of cauliflower mosaic virus, rd29A gene promoter, rbcS promoter, and mac-1 promoter.

Examples of the promoter inducibly activated by an external stimulus include a mouse mammary tumor virus (MMTV) promoter, a tetracycline-responsive promoter, a metallothionein promoter, and a heat shock protein promoter.

The plant to be transformed according to the present invention means any of the whole plant body, a plant organ (e.g., leaf, petal, stem, root, or seed), a plant tissue (e.g., cuticle, phloem, parenchyma, xylem, bundle, palisade tissue, or spongy tissue), a plant cultured cell, any of various forms of plant cells (e.g., a suspension cultured cell), a protoplast, a leaf segment, and a callus. The plant used for transformation is not particularly limited, and may be any of plants belonging to Liliopsida and Magnoliopsida.

Transformation methods well known to those of ordinary skill in the art (for example, an Agrobacterium method, a gene gun method, a PEG method, and an electroporation method) are used for the introduction of a gene into a plant. For example, a method through Agrobacterium and a method involving direct introduction into plant cells are well-known. When the Agrobacterium method is used, a transformed plant can be obtained by introducing a constructed expression vector for a plant into a suitable Agrobacterium strain (for example, Agrobacterium tumefaciens) and causing this strain to infect an aseptically cultured leaf disc according to a leaf disc method (Hirofumi Uchimiya, "Shokubutsu Idenshi Sosa Manyuaru (Plant genetic engineering manual)" (1990) p. 27-31, Kodansha Scientific, Tokyo, or the like). The method of Nagel et al. (Micribiol. Lett., 67: 325 (1990)) may be also used. This method is a method which involves first introducing, for example, an expression vector into Agrobacterium and then introducing the transformed Agrobacterium into a plant cell or a plant tissue by a method as described in Plant Molecular Biology Manual (Gelvin, S. B. et al., Academic Press Publishers). Here, "plant tissue" includes a callus obtained by the culture of plant cells. When transformation is carried out using the Agrobacterium method, a binary vector (pBI121, PZP202, or the like) can be used.

As the method involving directly introducing a gene into a plant cell or a plant tissue, an electroporation method and a particle gun method are known. When the particle gun is used, a plant body, a plant organ, or a plant tissue may be directly used, may be used after preparing the section thereof, or may be used by preparing a protoplast. The specimen thus prepared can be treated using a gene introduction device (for example, PDS-1000 (BIO-RAD Co., Ltd.)). Treatment conditions vary depending on the plant or the specimen; however, they are typically a pressure of on the order of 450 to 2,000 psi and a distance of on the order of 4 to 12 cm.

The gene-introduced cell or plant tissue is first selected by drug resistance, such as hygromycin resistance, and then regenerated into a plant body by an ordinary method. The regeneration of the plant body from the transformed cell can be carried out by a method known to those of ordinary skill in the art, depending on the type of the plant cell.

When cultured plant cells are used as a host, transformation is carried out by introducing a recombinant vector into the cultured cells by the gene gun or electroporation method or the like. The callus, shoot, hairy root, or the like obtained as a result of transformation can be directly used for cell culture, tissue culture or organ culture and can be regenerated into a plant body using a heretofore known plant tissue culture method, for example, by administering a suitable concentration of a plant hormone (e.g. auxin, cytokinin, gibberellin, abscisic acid, ethylene, or brassinoride).

Whether or not the polynucleotide of the present invention has been introduced into a plant can be confirmed using a PCR method, a Southern hybridization method, a Northern hybridization method, or the like. For example, DNA is prepared from a transformed plant, and primers specific for the DNA are designed to perform PCR. PCR can be carried out under the same conditions as those used for preparing the above plasmid. Thereafter, the amplified product can be subjected to agarose gel electrophoresis, polyacrylamide gel electrophoresis, or capillary electrophoresis, stained with ethidium bromide, SYBR Green solution or the like, and detected as a one band to confirm transformation. The amplified product can also be detected by performing PCR using primers labeled with a fluorescent dye or the like in advance. In addition, a method can be adopted which involves binding the amplified product to a solid phase, such as a microplate, and confirming the amplified product by fluorescence or enzyme reaction.

Once a transformed plant body in which the polynucleotide of the present invention is incorporated in the genome is obtained, an offspring can be obtained by the sexual reproduction or asexual reproduction of the plant body. From the plant body or its offspring or their clones, for example, a seed, a fruit, a cutting, a tuber, a root tuber, a stump, a callus, or a protoplast is obtained, and the plant body can be mass produced based on them. Thus, also included in the present invention is a plant body into which the polynucleotide according to the present invention is expressively introduced, an offspring of the plant body, having the same properties as those of the plant body, or tissues derived therefrom.

Transformation methods for various plants have already been reported. Examples of the transformant plant according to the present invention include Solanaceae plants (for example, eggplant, tomato, peppers, potato, tobacco, datura, nightshade, petunia, *Calibrachoa, Nierembergia*, etc.), Leguminosae plants (for example, soybean, azuki bean, peanut, kidney bean, broad bean, lotus, etc.), Rosaceae plants (for example, strawberry, plum, cherry, rose, blueberry, blackberry, bilberry, black currant, raspberry, *Rubus suavissimus*, etc.), Caryophyllaceae plants (carnation, gypsophila, etc.), Asteraceae plants (chrysanthemum, gerbera, sunflower, daisy, *stevia*, etc.), Orchidaceae plants (orchid, etc.), Primulaceae plants (cyclamen, etc.), Gentianaceae plants (lisianthus, gentian, etc.), Iridaceae plants (freesia, iris, gladiolus, etc.), Scrophulariaceae plant (snapdragon, Torenia, etc.), Crassulaceae (kalanchoe), Liliaceae plants (lily, tulip, etc.), Convolvulaceae plants (morning glory, ipomoea cairica, moonflower, sweet potato, cypress vine, evolvulus, etc.), Hydrangeaceae plants (hydrangea, deutzia, etc.), Cucurbitaceae plants (cucumber, bitter gourd, pumpkin, loofah, *Siraitia grosvenorii*, bottle gourd, etc.), Geraniaceae plants (Pelargonium, geranium, etc.), Oleaceae plants (forsythia, etc.), Vitaceae plants (for example, grape, etc.), Theaceae plants (camellia, tea, etc.), Gramineae plants (for example, rice, barley, wheat, oat, rye, corn, millet, Japanese millet, kaoliang, sugar cane, bamboo, wild oat, finger millet, sorghum, wild rice, pearl barley, pasture grass, etc.), Moraceae plants (mulberry, paper mulberry, rubber tree, hemp, etc.), Rubiaceae plant (Coffea, gardenia, etc.), Fagaceae plants (oak, beech, Kashiwa oak, etc.), Pedaliaceae plants (sesame, etc.), Rutaceae plants (for example, bitter orange, citron, satsuma mandarin, Japanese pepper) and Brassicaceae plants (red cabbage, ornamental cabbage, Japanese radish, *Arabidopsis thaliana, Brassica rapa* L. var. nippo-oleifera, cabbage, broccoli, cauliflower, etc.), Labiatae (salvia, beefsteak plant, lavender, skull cap, etc.), and Cannabaceae (hop, etc.). Particularly preferred examples of the plant to be transformed used are plants known to biosynthesize various glycosides using mogrol or a mogrol glycoside as a sugar receptor; examples of such plants include *Siraitia grosvenorii* and *Rubus suavissimus*.

The plant body transformed with the polynucleotide of the present invention (hereinafter referred to as "plant of the present invention" or "plant body of the present invention") can produce a large amount of a mogrol glycoside compared to its wild type one if it has a suitable substrate or if a suitable substrate is externally added.

The plant of the present invention can easily provide a complete plant body by the cultivation of seeds, cuttings, bulbs, or the like of the plant of the present invention.

Thus, included in the plant of the present invention are included the whole plant body, plant organs (e.g., leaf, petal, stem, root, seed, and bulb), plant tissues (e.g., cuticle, phloem, parenchyma, xylem, bundle, palisade tissue, and spongy tissue), plant cultured cells, various forms of plant cells (e.g., suspension cultured cells), protoplasts, leaf segments, calluses, and the like.

4. Transformant Extract and Use Thereof

In another embodiment, the present invention provides an extract of the above transformant. The transformant of the present invention has a high content of a mogrol glycoside compared to its wild type one if it has a suitable substrate or if a suitable substrate is externally added; thus, the mogrol glycoside is probably contained in a high concentration in its extract.

The extract of the transformant of the present invention can be obtained by crushing the transformant using, for example, glass beads, a homogenizer, or a sonicator, subjecting the crushed product to centrifugal treatment, and recovering the supernatant. In addition, a further extraction step may be provided using the above-described method for extracting a mogrol glycoside.

The extract of the transformant of the present invention can be used in applications of, for example, the production of a food, a pharmaceutical product, or an industrial raw material and the like according to an ordinary method.

In another embodiment, the present invention provides a food, a medicine, and an industrial raw material (a raw material for foods or the like) which contain the extract of the transformant of the present invention. The food, medicine, and industrial raw material containing the extract of the transformant of the present invention are prepared according to ordinary methods. Thus, the food, medicine, industrial raw material, or the like containing the extract of the transformant of the present invention contains a mogrol glycoside formed using the transformant of the present invention.

The dosage form of the pharmaceutical product (composition) of the present invention is not particularly limited and may be any dosage form, such as solutions, pastes, gels, solids, or powders. The pharmaceutical composition of the present invention can be used in bath agents, hair tonics, skin beauty liquids, sunscreen agents, and the like in addition to medicines for external use, such as oils, lotions, creams, emulsions, gels, shampoos, hair rinses, hair conditioners, enamels, foundations, lipsticks, face powders, packs, ointments, powders, dentifrices, aerosols, and cleansing foams.

The pharmaceutical composition of the present invention may further contain other pharmaceutically active ingredients (for example, an anti-inflammatory ingredient) or auxiliary components (for example, a lubricating component and a carrier component), if necessary.

Examples of the food of the present invention include a dietary supplement, a health food, a functional food, an infant food, and a geriatric food. The food herein is a solid, a fluid, a liquid, or a mixture thereof, and is a generic term applied to ingestible materials.

The dietary supplement refers to a food in which specific nutritional ingredients are enriched. The health food refers to a food which is healthy or considered to be good for the health, and includes a dietary supplement, a natural food, and a diet food. The functional food refers to a food for replenishing nutritional ingredients performing body control functions, and is the same meaning as a food for specified health use. The infant food refers to a food for giving to children up to about 6 years old. The geriatric food refers to a food treated so as to be easily digested and absorbed compared to the untreated food.

The food of the present invention uses a mogrol glycoside, which is a calorie-less sweetener. Thus, the food of the present invention has the merit of being low in calories and contributing to health promotion or health maintenance.

Examples of the form of these foods may be agricultural food products, such as bread, noodles, pasta, rice, confectionery (cakes, ice cream, ice candy, doughnut, baked cakes, candy, chewing gum, gummi, tablet confectionery, and Japanese sweets (e.g., dumplings and buns with a bean-jam filling)) and tofu and its processed products; fermented foods, such as sake, medicinal beverage, sweet sake, vinegar, soy sauce, and miso; livestock products, such as yogurt, ham, bacon, and sausage; sea foods, such as boiled fish paste, fried fish-meat paste, and boiled flat fish cake; and juice drinks, soft drinks, sports beverages, alcoholic beverages, teas, or seasonings.

5. Method of Screening for Plant Having High Mogrol Glycoside Content

The present invention provides a method of screening for a plant having a high mogrol glycoside content. Specifically, the method includes the following (1) to (3) steps:

(1) a step of extracting mRNA from a test plant;

(2) a step of hybridizing the mRNA or cDNA prepared from the mRNA with a polynucleotide capable of hybridizing with a polynucleotide consisting of a nucleotide sequence complementary to the polynucleotide of the present invention under highly stringent conditions; and (3) a step of detecting the above hybridization.

The above step (1) can be carried out by extracting mRNA from a test plant. The part of a test plant from which mRNA is extracted is not particularly limited; however, it is preferably a petal. When mRNA has been extracted, cDNA may be prepared from the mRNA by reverse transcription.

The step (2) can be carried out by hybridizing the extracted mRNA with a polynucleotide or oligonucleotide consisting of a nucleotide sequence complementary to the polynucleotide of the present invention as a probe or primer under highly stringent conditions. The highly stringent conditions are as already described. The polynucleotide or oligonucleotide preferably has a length of 5 to 500 bp, more preferably 10 to 200 bp, still more preferably 10 to 100 bp. The polynucleotide or oligonucleotide can be easily synthesized using any of various automated synthesizers (for example, AKTA oligopilot plus 10/100 (GE Health Care)), or can also be synthesized under commission to a third-party organization (for example, Promega or Takara) or the like.

When the polynucleotide consisting of a nucleotide sequence complementary to the polynucleotide of the present invention is used as a probe in the step (2), the step (3) can be carried out by a hybridization detection method, such as conventional Southern blotting, Northern blotting (Sambrook, Fritsch and Maniatis, "Molecular Cloning: A Laboratory Manual" 2nd Edition (1989), Cold Spring Harbor Laboratory Press), microarray (Affymetrix Co., Ltd.; see U.S. Pat. Nos. 6,045,996, 5,925,525, and 5,858,659), TaqMan PCR (Sambrook, Fritsch and Maniatis, "Molecular Cloning: A Laboratory Manual" 2nd Edition (1989), Cold Spring Harbor Laboratory Press), or fluorescent in situ hybridization (FISH) (Sieben V. J. et al., (2007-06), IET Nanobiotechnology 1(3): 27-35). When the polynucleotide consisting of a nucleotide sequence complementary to the polynucleotide of the present invention is used as a primer in the step (2), the hybridization detection in the step (3) can be carried out by performing PCR amplification reaction and analyzing the resultant amplified product by electrophoresis or sequencing (Sambrook, Fritsch and Maniatis, "Molecular Cloning: A Laboratory Manual" 2nd Edition (1989), Cold Spring Harbor Laboratory Press).

A plant body for which more hybridization is detected can be said to express a larger amount of a protein having an activity of adding a sugar molecule to an $R^1$ group at position 24 of a compound represented by the following formula (I) than that for other plant bodies, and thus is expected to have a high mogrol glycoside content.

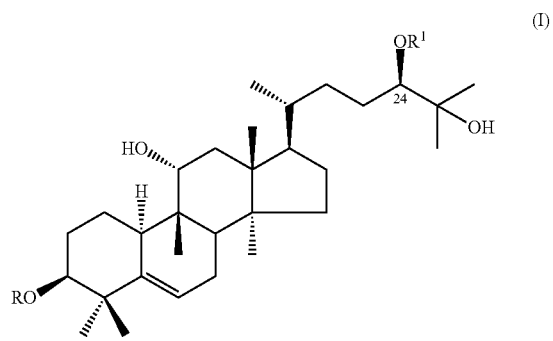

(I)

EXAMPLES

The present invention will be more specifically described below with reference to Examples. However, the scope of the present invention is not intended to be limited to such Examples.

Example 1: Isolation of Candidate Gene of Mogrol Glycosyltransferase

The molecular biological technique used in this Example was according to the method described in Molecular Cloning (Sambrook et al., Cold Spring Harbor Laboratory Press, 2001) until detailed otherwise.

Tanscriptome analysis (RNA-sequencing) for the fruit of *Siraitia grosvenorii* using a next-generation sequencer (NGS) has been published (Tang, Q. et al. (2011) MC Genomics 12: 343); for the sequence information, sequences having high identity to the known glycosyltransferase were selected by identity analysis using blastn.

Example 2: Functional Analysis of Candidate Gene

Figure 2:
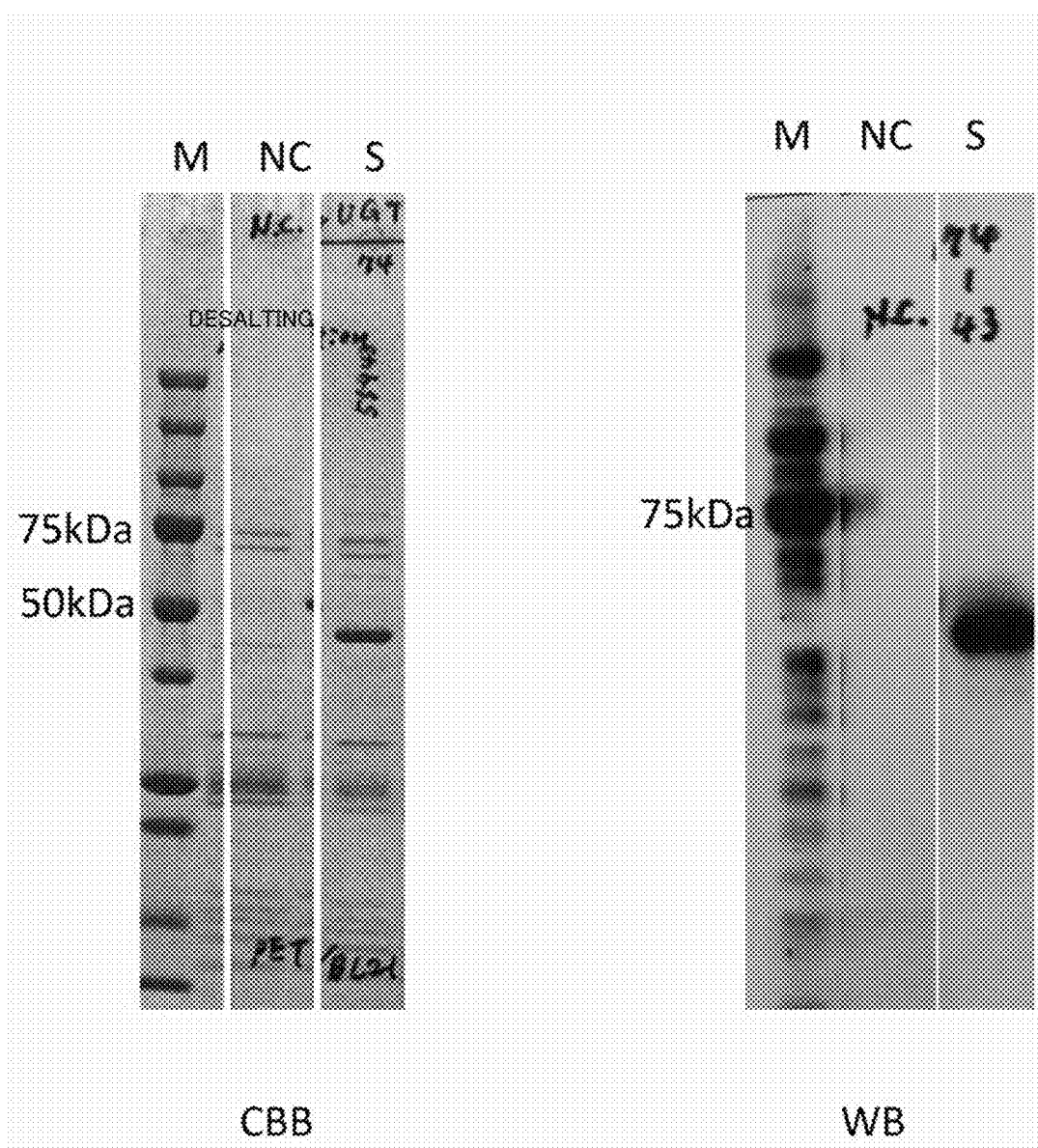
FIG. 2 is a set of photographs showing the expression of SgUGT74G1_943 protein.

Based on the sequence information of SgUGT74G1_943, one of the resultant candidate genes, (SEQ ID NO: 1), SgUGT74G1_943 gene was artificially synthesized in ThermoFiosher Co., Ltd. The resultant synthetic gene fragment was incorporated into the restriction enzyme sites NdeI and BamHI of an *E. coli* expression vector, pET15b (Novagen Co., Ltd.), and designed so that HisTag is fused to the N-terminal. The vector was transformed into *E. coli* (BL21_DE3) according to an ordinary method, and a recombinant protein was expressed using the Overnight Express™ autoinduction system from Millipore Co., Ltd. according to the protocol provided by the manufacturer. The expression of the recombinant protein could be confirmed as a band of around 50 kDa as deduced by CBB staining and Western blot analysis with a mouse anti-HiSTag antibody (FIG. 2). FIG. 2 shows the results of expression analysis of the recombinant protein by Coomassie brilliant blue staining (CBB: left Figure) and Western blotting analysis (WB: right Figure); in the figure, M represents a size marker, NC represents negative control (pET15b/BL21 (strain DE3)), and S represents a sample (SgUGT74G-943/pEt15b/BL21 (strain DE3)).

Purification was carried out using the HisTag of the recombinant protein according to an ordinary method, and glucose transfer activity for mogrol prepared by hydrolyzing a *Siraitia grosvenorii* extract (Takemoto, T. et al. (1983) YAKUGAKU ZASSHI 103(11), 1167-1173) was evaluated. The enzyme reaction composition was 0.2 mM mogrol as a glucose acceptor, 2 mM UDP-glucose as a glucose donor, and 50 mM calcium phosphate buffer (pH 7.5); an enzyme solution was added thereto, which was then reacted at 30° C. for 3 hours; and the product was analyzed using LC-IT-TOF-MS (Shimadzu Corporation).

Figure 3:
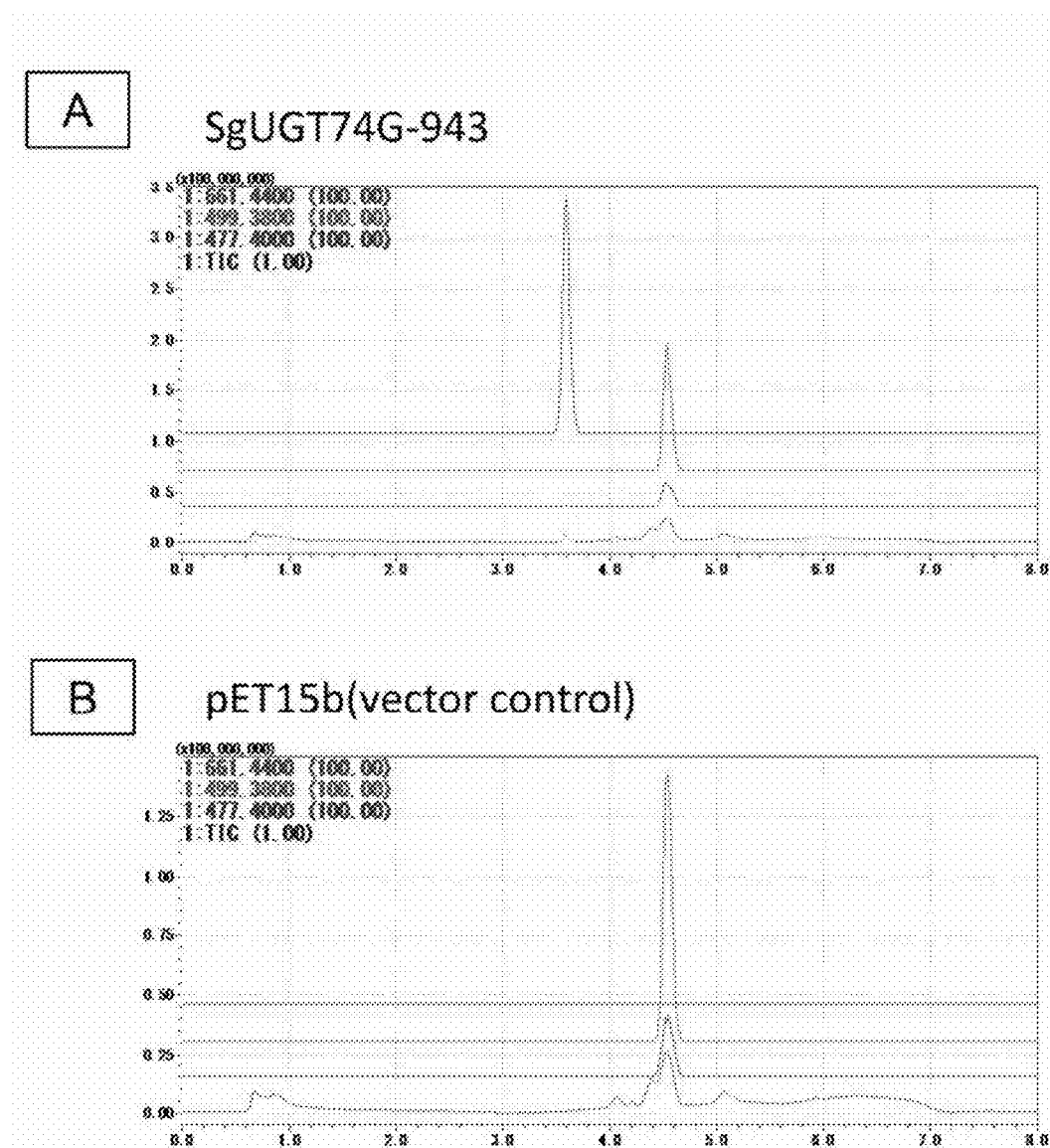
FIG. 3 is an LC-MS analysis chart of a mogrol glycoside formed by the glycosylation activity of SgUGT74G1_943 protein.

As a result, a new product was observed in addition to mogrol in the reaction solution of SgUGT74G_943 enzyme (FIG. 3). FIG. 3A is an LC-MS analysis chart of the reaction solution between SgUGT74G_943 and mogrol; the red line represents a Na adduct ion of mogrol having one molecule of glucose added corresponding to m/z=661, the pink line represents a Na adduct ion of mogrol corresponding to m/z=499, the blue line represents a proton adduct of mogrol corresponding to m/z=477, and the black line represents TIC (total ion chromatography of positive ions).

Aside from mogrol as a substrate, no peak of a product was observed in the reaction solution of the vector control (FIG. 3B). In the LC-MS analysis chart for the reaction solution of the negative control expressing an empty vector in FIG. 3B, ion peak derived from mogrol was only observed. The product was concluded to be mogrol monoglycoside in which one molecule of glucose was added by SgUGT74_943, from its mass and retention time. The sugar-binding site was found to be position 24 of mogrol from comparison with past references (Ukiya, M., et al. (2002) J. Agric. Food. Chem. 50, 6710-6715 and Takemoto, T. et al. (1983) YAKUGAKU ZASSHI 103(11), 1167-1173), which used nuclear magnetic resonance (NMR).

Example 3: Activity Comparison with Known Enzyme

It has heretofore been known that a steviol glycosyltransferase derived from *stevia* can glycosylate mogrol (WO2013/076577). Then, the mogrol glycosylation activity of *Siraitia grosvenorii*-derived SgUGT74-943 was compared with the same activities of UGT85C2 and UGT73E1 of *stevia*.

Figure 4:
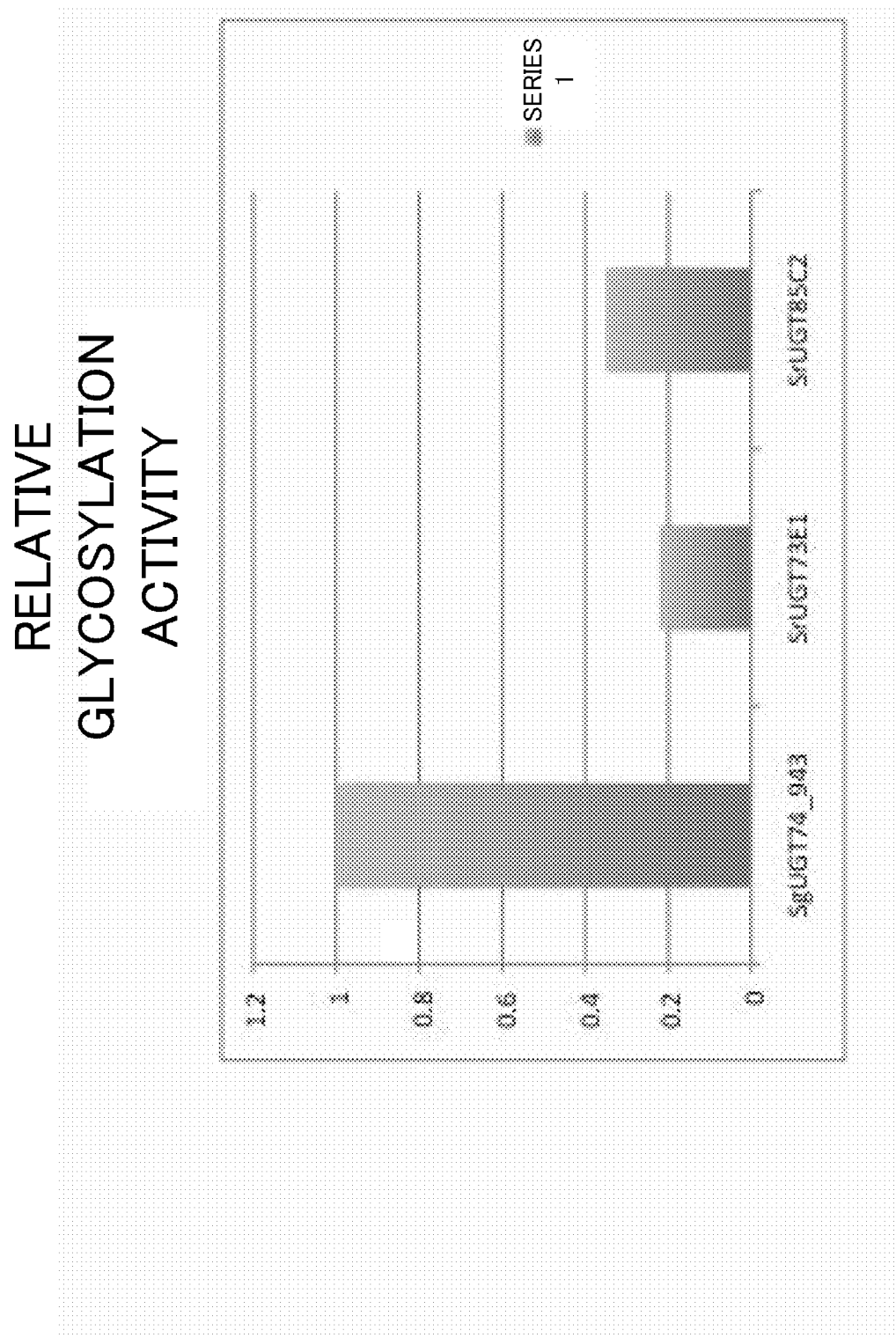
FIG. 4 is a graph showing the relative activities of *stevia* (Sr)-derived UGT73E1 and UGT85C2 when the activity of *Siraitia grosvenorii* (Sg)-derived UGT74G-943 is set to 1.

*Stevia*-derived UGT85C2 and UGT73E1 were expressed in the same manner as in the above method. The product amount was measured under the above enzyme conditions to determine relative activity by dividing it by the expressed protein amount. As a result, the relative activities of *stevia*-derived UGT85C2 and UGT73E1 when the activity of SgUGT74-943 was set to 1 were 0.35 and 0.22, respectively. The glycosylation activity of *Siraitia grosvenorii*-derived SgUGT74-943 was confirmed to be nearly 3 times higher than those of *stevia*-derived UGT85C2 and UGT73E1 (FIG. 4).

INDUSTRIAL APPLICABILITY

The gene of an enzyme glycosylating position 24 of mogrol was found out from *Siraitia grosvenorii*. The present invention can be used not only for such breeding as to increase the mogrol glycoside content using the gene as an index but also for the study of environmental conditions for increasing the mogrol glycoside content in cultivation and in post-harvest. In addition, it can be used as a tool, such as an external enzyme, for the production of a useful substance.

We claim:
1. A polynucleotide selected from:
   (a) a polynucleotide comprising the nucleotide sequence of SEQ ID NO: 1;
   (b) a polynucleotide comprising a heterologous regulatory element operably linked to a polynucleotide sequence encoding a protein consisting of the amino acid sequence of SEQ ID NO: 2; and
   (c) a polynucleotide encoding a protein consisting of an amino acid sequence in which 1 to 45 amino acids are deleted, substituted, inserted, and/or added in the amino acid sequence of SEQ ID NO: 2 and having an activity of adding a sugar molecule to an $R^1$ group at position 24 of a compound represented by the formula (I)

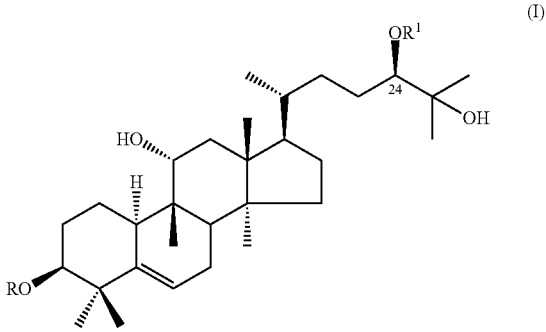

where R and $R^1$ each independently represent H, a monosaccharide, or a disaccharide.

2. A protein consisting of an amino acid sequence in which 1 to 45 amino acids are deleted, substituted, inserted, and/or added in the amino acid sequence of SEQ ID NO: 2 and having an activity of adding a sugar molecule to an R1 group at position 24 of a compound represented by formula (I)

where R and $R^1$ each independently represent H, a monosaccharide, or a disaccharide.

3. A vector comprising the polynucleotide of claim 1.

4. A non-human transformant comprising the polynucleotide of claim 1.

5. The non-human transformant of claim 4, which is a plant or a microorganism.

6. The non-human transformant of claim 4, wherein the polynucleotide is inserted into an expression vector.

7. A method comprising culturing or cultivating the non-human transformant of claim 4 to produce the protein consisting of the amino acid sequence of SEQ ID NO: 2.

8. The method of claim 7, further comprising:
   producing a mogrol glycoside by reacting the protein consisting of the amino acid sequence of SEQ ID NO: 2 produced by the non-human transformant with a UDP-sugar and a compound represented by formula (I):

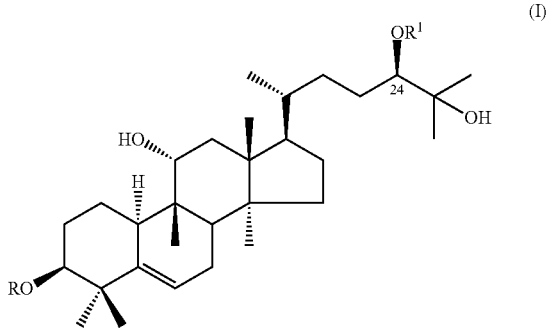

where R and R¹ each independently represent H, a monosaccharide, or a disaccharide.

9. A method of producing a mogrol glycoside, comprising:
reacting in vitro a protein consisting of the amino acid sequence of SEQ ID NO: 2 with a UDP-sugar and a compound represented by formula (I):

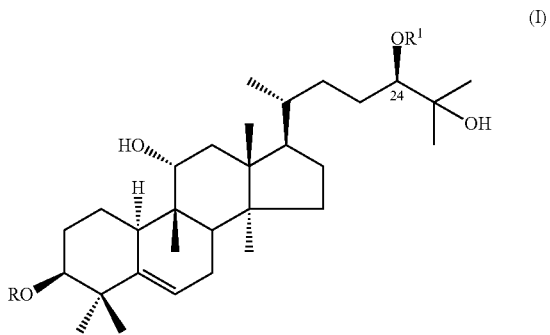

where R and R¹ each independently represent H, a monosaccharide, or a disaccharide.

10. A method comprising:
providing the non-human transformant of claim 4 or a culture thereof, and
obtaining an extract of the non-human transformant or of the culture of the non-human transformant.

11. A method comprising:
providing an extract of the non-human transformant of claim 4 or an extract of a culture of the non-human transformant of claim 4,
adding the extract to a raw material of a food, a pharmaceutical preparation or an industrial raw material, and
preparing a food, a pharmaceutical preparation or an industrial raw material.

12. The method of claim 8, wherein the UDP-sugar is a UDP-hexose.

13. The method of claim 8, wherein the sugar molecule is selected from the group consisting of UDP-glucose, UDP-mannose, and UDP-galactose.

14. The method of claim 8, wherein R and R¹ is each independently H or a sugar residue of a glucose monomer or a glucose dimer.

15. The method of claim 8, wherein the compound represented by formula (I) is mogrol or a mogrol glycoside.

16. The method of claim 8, wherein the mogrol glycoside is mogroside IA, mogroside Ib, mogroside IE, mogroside IIA, mogroside IIA1, mogroside IIE, mogroside III, mogroside IIIA1, mogroside IIIA2, mogroside IIIE, mogroside IV, mogroside IVA, mogroside V, siamenoside I, 11-oxomogroside V, mogrol pentaglycoside, or a combination thereof.

17. The method of claim 9, wherein the mogrol glycoside is mogroside IA, mogroside Ib, mogroside IE, mogroside IIA, mogroside IIA1, mogroside IIE, mogroside III, mogroside IIIA1, mogroside IIIA2, mogroside IIIE, mogroside IV, mogroside IVA, mogroside V, siamenoside I, 11-oxomogroside V, mogrol pentaglycoside, or a combination thereof.

18. The method of claim 11, wherein the food is a beverage.

19. The method of claim 11, wherein the food is selected from a juice drink, a soft drink, a sports beverage, an alcoholic beverage, a tea, a vinegar, and a soy sauce.

* * * * *